United States Patent
Iizuka et al.

(10) Patent No.: US 7,133,127 B2
(45) Date of Patent: Nov. 7, 2006

(54) LIGHTING OPTICAL MACHINE AND DEFECT INSPECTION SYSTEM

(75) Inventors: Masami Iizuka, Ishioka (JP); Shigeru Matsui, Hitachinaka (JP); Tadashi Suzuki, Kasama (JP); Hiroshi Goto, Ushiku (JP); Takayuki Ono, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 412 days.

(21) Appl. No.: 10/612,148

(22) Filed: Jul. 3, 2003

(65) Prior Publication Data

US 2004/0008341 A1    Jan. 15, 2004

(30) Foreign Application Priority Data

Jul. 10, 2002    (JP)    ............... 2002-200720

(51) Int. Cl.
*G01N 21/00*    (2006.01)
(52) U.S. Cl. ................. 356/237.1; 356/237.2
(58) Field of Classification Search ............. None
See application file for complete search history.

(56) References Cited

U.S. PATENT DOCUMENTS

| 6,490,047 B1 * | 12/2002 | Siu ........................ 356/502 |
| 6,512,843 B1 | 1/2003 | Kuwabara | |
| 6,831,737 B1 * | 12/2004 | Uto et al. ............. 356/237.4 |
| 2003/0020904 A1 * | 1/2003 | Uto et al. ............. 356/237.2 |

FOREIGN PATENT DOCUMENTS

| JP | 05-289116 | 11/1993 |
| JP | 08-035937 | 2/1996 |
| JP | 08-184407 | 7/1996 |
| JP | 09-005251 | 1/1997 |
| JP | 2000-131240 | 5/2000 |
| JP | 2001-141428 | 5/2001 |
| JP | 2002-022415 | 1/2002 |
| JP | 2002-39959 | 2/2002 |
| JP | 2002-116361 | 4/2002 |

\* cited by examiner

*Primary Examiner*—Michael P. Stafira
(74) *Attorney, Agent, or Firm*—Dickstein Shapiro LLP

(57) ABSTRACT

A lighting optical machine and defect inspection system having high reliability and safety when a laser beam is used as a light source. The lighting optical machine comprises: a housing, which accommodates a laser source, a beam polarization mechanism having first and second plane mirrors enabling a beam emitted from the laser source to be reflected so that the beam travels in the direction almost parallel to the beam emitted from the laser source, a beam expander for converting the beam to a parallel beam having a larger cross-sectional area, an objective lens, through which the parallel beam is reduced and applied to the surface of a sample; a first control mechanism for controlling the directions of the two plane mirrors of the beam polarization mechanism with an electric signal; and a second control mechanism for controlling the focus position of the beam expander with an electric signal.

2 Claims, 3 Drawing Sheets

US 7,133,127 B2

LIGHTING OPTICAL MACHINE AND DEFECT INSPECTION SYSTEM

BACKGROUND OF THE INVENTION

1. Technical Field

The present invention relates to a lighting optical machine and a defect inspection system used for the inspection or observation of critical dimensional pattern defects and foreign matters typically found in manufacturing processes of semiconductor devices or flat panel displays.

2. Background Art

As semiconductors are highly integrated, circuit patterns tend to be finer than ever. Under these circumstances, higher and higher resolution is required for detecting defects of circuit patterns on wafers, which are lithographed through exposure from circuit patterns formed on masks or reticles for use in photolithography processes for manufacturing semiconductors. In order to enhance the resolution, a lighting beam may be changed from visible light to ultraviolet light so that the beam has a shorter wavelength. Conventionally, an Hg lamp has been used as a light source, and among various emission lines generated from an Hg lamp, those with required wavelengths have been optically selected for use. However, the emission lines of the Hg lamp have a broader emission spectrum and it is difficult to correct optical color aberrations thereof. Further, in order to obtain sufficient illuminance, a large light source is necessary, resulting in decreased efficiency.

In recent years, an exposure device carrying a KrF excimer laser with a wavelength of 248 nm as a light source therefor in the semiconductor manufacturing processes has been developed. However, the excimer laser light source is large and predetermined safety measures must be taken due to the use of fluorine gas.

Examples of ultraviolet laser light sources include a laser device wherein the wavelength of a solid-state YAG laser light is converted with a nonlinear optical crystal and an Ar—Kr laser device, and a laser beam with the wavelength of 266 or 355 nm can be obtained thereby. It is advantageous that these laser devices have a larger output power in comparison with lamps conventionally used as light sources, and generate a parallel pencil, the beam passage of which can freely be routed. On the other hand, due to the coherence properties of lasers, laser speckle occurs, and causing adverse influences such as uneven brightness in detecting the circuit patterns formed on a sample. Incidentally, JP Patent Publication (Kokai) No. 2001-141428 A discloses a solution to this problem as a conventional technology. However, the technology of the above publication is not directed at reliability regarding the detection accuracy, such as optical axis adjustment and luminous energy adjustment, or at safety during the use of a laser.

SUMMARY OF THE INVENTION

An object of the present invention is to provide a lighting optical machine and a defect inspection system having high reliability and safety when a laser beam is used as a light source.

According to an embodiment of the present invention, a lighting optical machine comprises:

a housing, wherein the housing accommodates a laser source, a beam deflection mechanism having a first and a second plane mirrors, which enable a beam emitted from the laser source to be reflected so that the beam travels in the direction almost parallel to the beam emitted from the laser source, a beam expander for converting the beam to a parallel beam having a larger cross sectional area, and an objective lens, through which the parallel beam is reduced and applied to the surface of a sample;

a first control mechanism for controlling the directions of the two plane mirror of the beam polarization mechanism with an electric signal; and a second control mechanism for controlling the focus position of the beam expander with an electric signal, A further embodiment of the present invention is a pattern defect inspection system provided with the above lighting optical machine.

This specification includes part or all of the contents as disclosed in the specification and/or drawings of Japanese Patent Application No. 2002-200720, which is a priority document of the present application.

BRIEF DESCRIPTION OF THE INVENTION

DESCRIPTION OF THE INVENTION

Figure 1:
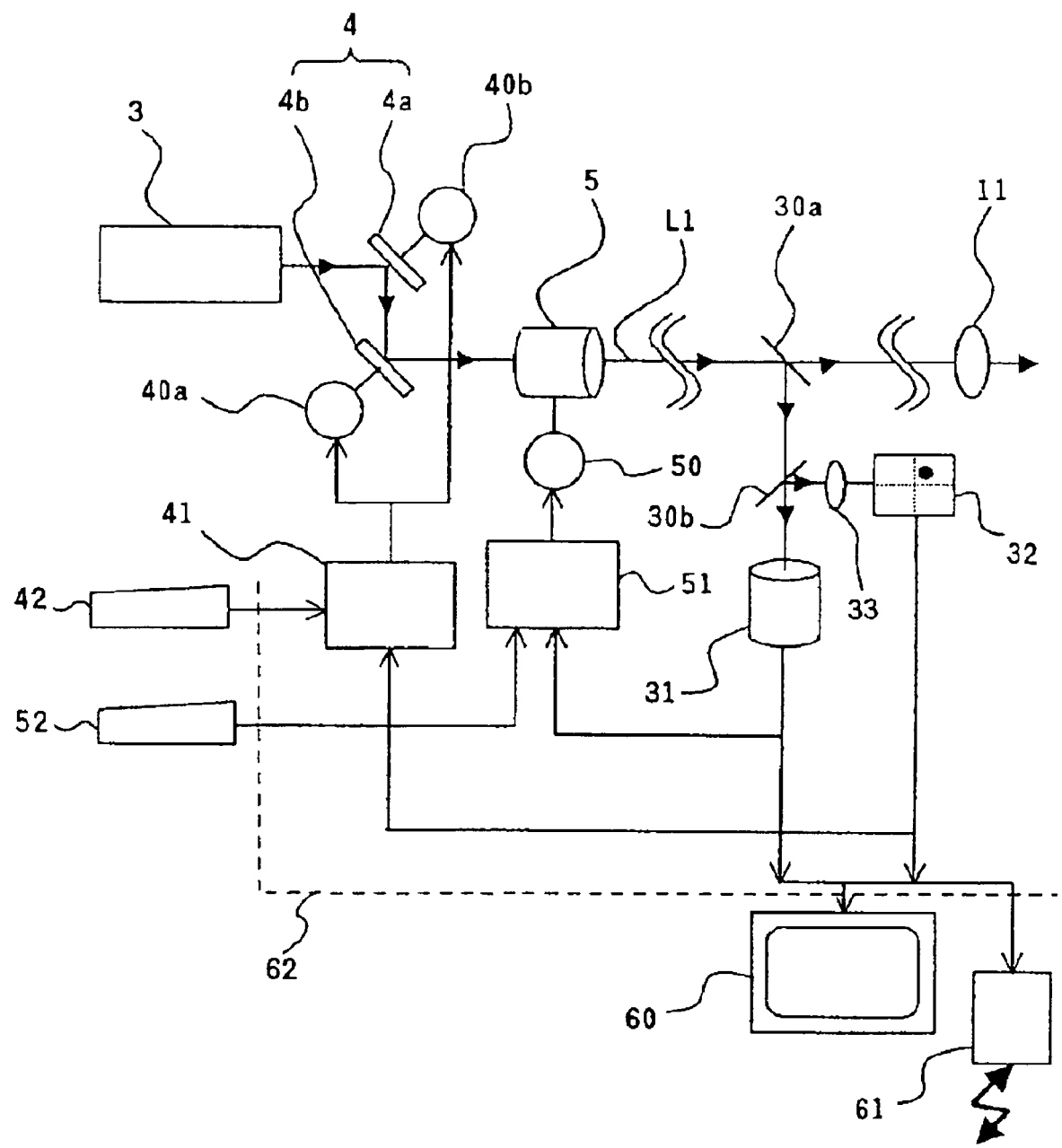
FIG. 1 is a view showing the configuration of a lighting optical mechanism according to the present invention.

Hereinafter, embodiments of the present invention will be described with reference to FIGS. 1 to 3. FIG. 1 shows one exemplary configuration of a lighting optical system according to the present invention. In the present invention, in order to accomplish high brightness lighting in a short wavelength area, a far ultraviolet laser beam is used as a laser beam source 3. A laser beam L1 emitted (oscillated) from the laser beam source 3 changes its angle at a first plane mirror 4a and changes its angle again at a second plane mirror 4b so as to be almost parallel to a beam emitted from the laser beam source 3.

Next, a beam expander 5 enables the laser beam L1 to become a parallel pencil having a large cross-sectional diameter. The beam then enters into an objective lens 11 through a low coherent optical unit, a beam splitter for polarization, polarization devices, or the like, with which an object to be measured is irradiated. The laser beam L1 expanded by the beam expander 5 is converged around the pupil of the objective lens 11 with a lens on the way to the objective lens 11, and thereafter used for Kohler's illumination on a sample.

Further, the first and second plane mirrors 4a and 4b are coupled to a beam deflection mechanism 40a and 40b, respectively, which are driven by a motor, etc. to change the angle of the plane mirrors. Furthermore, they are connected to a beam polarization mechanism control part 41 for controlling their angles. Moreover, the beam polarization mechanism control part 41 is coupled to a manual operation input part 42, through which the polarization angle can be manually controlled.

In addition, the beam expander 5 is coupled to a beam expander adjustment mechanism 50 driven by a motor, etc., and the beam can be changed to a parallel pencil having an enlarged cross-sectional diameter by changing the focus position. Further, it is connected to a beam expander adjustment mechanism control part 51 to control the size of the cross-sectional diameter. The beam expander adjustment mechanism control part 51 is connected to a manual operation input part 52, through which the size of cross-sectional diameter of the beam can be manually controlled.

Also, a first beam splitter 30a is provided after the beam expander 5 for amplitude splitting of the parallel pencil, which is further divided in two with a second beam splitter 30b. One of the divided beams enters into a beam profile observation camera 31 so that the beam shape thereof is obtained. Using the obtained shape, the beam cross-sectional diameter can be measured. Thus, when the obtained value is not that of a predetermined cross-sectional diameter, an instruction is sent to the beam expander adjustment mechanism control part 51 to adjust the cross-sectional diameter. Based on the instruction, the beam cross-sectional diameter is automatically adjusted to achieve the predetermined value.

The other divided beam passes through a convergence lens 33 and is converged on a beam spot positioning sensor 32 so that a beam position displacement is detected. When a position displacement is found, an instruction to adjust the beam position to the center is sent to the beam polarization mechanism control part 41. Based on the instruction, the beam spot position is automatically adjusted to the center. As described above, it is possible to maintain a constantly stable light beam.

Additionally, there may be provided a display monitor 60, which monitors information from the beam profile observation camera 31 and beam spot positioning sensor 32, or a communication means 61.

All portions except the manual operation input parts 42 and 52 are accommodated in a housing 62, and thereby there is no fear of a laser beam leaking outside. When the laser beam is adjusted, the position, angle, or cross-sectional diameter of the beam can be adjusted with the manual operation input parts 42 and 52 present outside the housing 62, so that there is no chance that an operator may be exposed to the laser beam and the laser beam can be adjusted by remote control. The housing 62 may have a structure such as a shape for covering all portions except the manual input parts 42 and 52. It may also have a shape with sleeve-shaped members for covering beam passages and a slightly larger covering part for the lens, etc. Further, it is not necessary to conduct operations in a limited narrow space, and an operator can conduct operations through remote control, so that the labor of the operator can be reduced. It is preferable to install the display monitor 60 or communication means 61 outside the housing 62.

Figure 2:
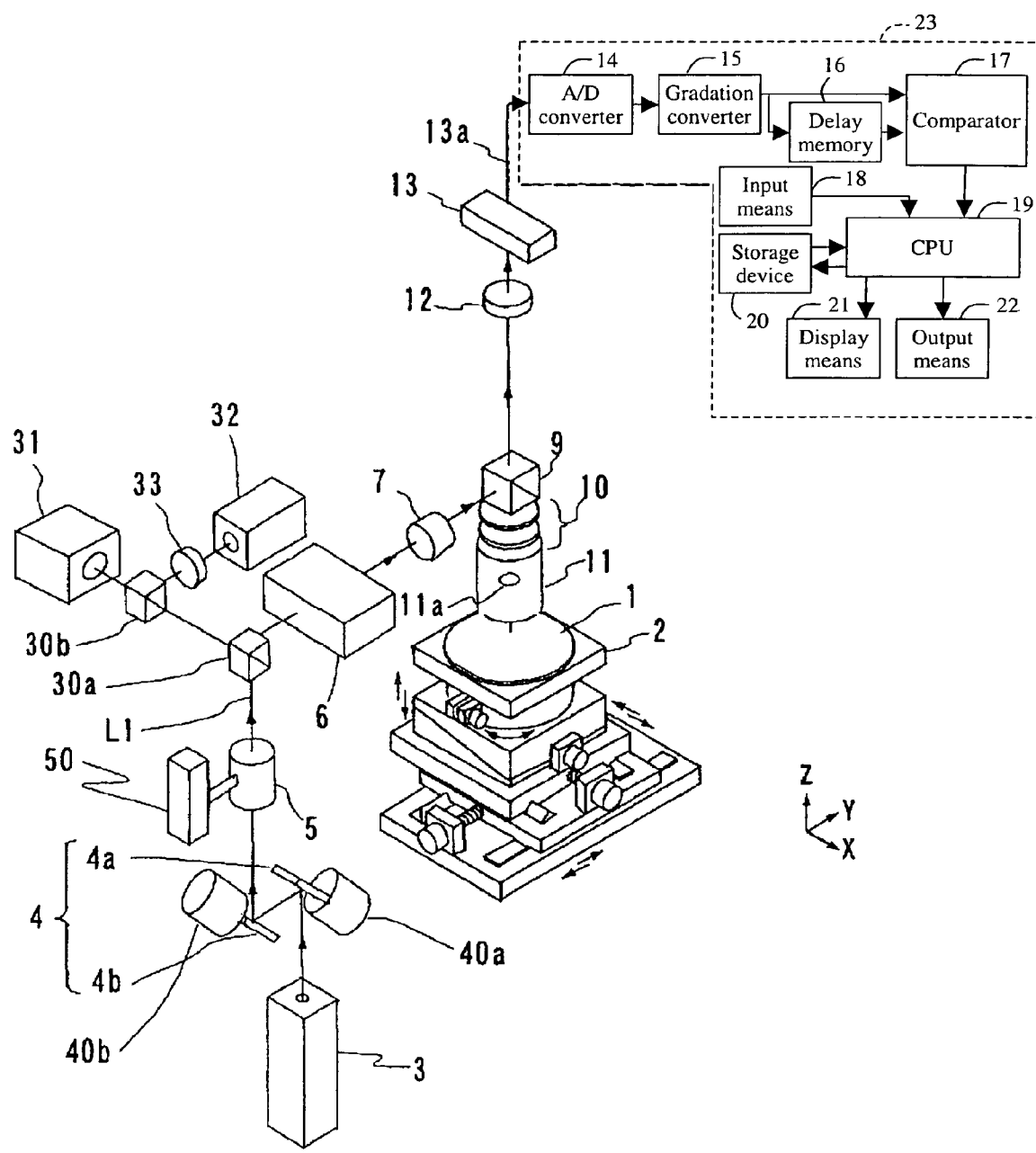
FIG. 2 is a perspective view showing the configuration of a mechanical part of an optical wafer defect inspection.
Figure 3:
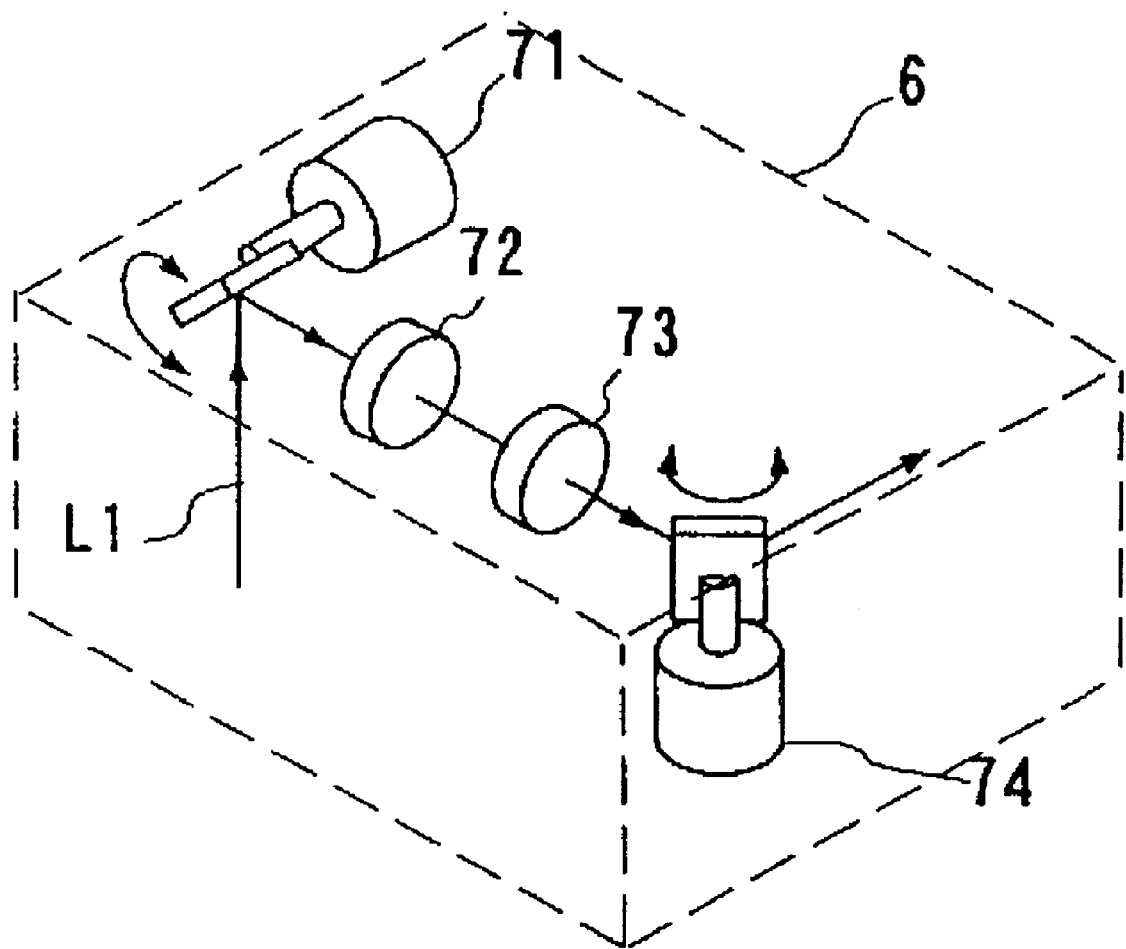
FIG. 3 is a perspective view showing the configuration of a low coherent optical unit 6.

Next, FIG. 2 shows one exemplary configuration of a lighting optical mechanism of an optical wafer defect inspection system as an apparatus provided with the above lighting optical machine. However, the figure partially contains a flow chart regarding the image processing mechanism. In the present invention, a ultraviolet laser beam is used as a light source to achieve high brightness in a short wavelength area.

A stage 2 has degrees of freedom in directions of the X, Y, Z, and θ axes, and a semiconductor wafer 1 having one example pattern to be inspected is mounted as a sample. The laser beam L1 emitted from the laser beam source 3 enters into the objective lens 11 through a mirror 4 comprising a first plane mirror 4a and a second plane mirror 4b, a beam expander 5, a low coherent optical unit 6, a lens 7, a polarization beam splitter 9, and polarization devices 10. It is then applied to the semiconductor wafer 1 as one example pattern to be inspected.

The beam expander 5 expands a laser beam to a certain size. The expanded laser beam L1 is converged in the vicinity 11a of the pupil of the objective lens 11 with the lens 7, and thereafter used for Kohler's illumination on the sample.

Further, the first plane mirror 4a and the second plane mirror 4b are coupled to beam polarization mechanisms 40a and 40b in order to change their angles. The beam expander 5 is also coupled to a beam expander adjustment mechanism 50 capable of changing its focus position. Furthermore, a first beam splitter 30a is provided after the beam expander 5 for amplitude-splitting of a parallel pencil, and a second beam splitter 30b separates the beam in two. One of the divided beams enters into a beam profile observation camera 31 so that the shape of the beam is obtained. The other divided beam passes through a convergence lens 33 and is converged on a beam spot positioning sensor 32 so that a beam position displacement is detected.

A reflecting beam from the sample is detected with an image sensor 13 via the objective lens 11, the polarization devices 10, the polarization beam splitter 9, and an image formation lens 12, which are arranged vertically from above the sample. The polarization beam splitter 9 reflects the beam, when the polarization direction of the leaser beam is parallel to its reflecting face. When the direction is perpendicular to the reflecting face, the splitter allows the beam to be transmitted therethrough. The laser beam used as a light source is originally a polarization laser, and the polarization beam splitter 9 is installed so as to reflect all the laser beams.

Meanwhile, the pattern to be inspected, which has been formed on the wafer 1 through semiconductor processes, exhibits various shapes. Therefore, a reflecting beam from the pattern has various polarization components. The polarization devices 10 control the polarization direction of the laser lighting beam and reflecting beam so as to have a function to arbitrarily adjust a polarization ratio of the lighting beam. The function prevents uneven brightness of the reflecting beam caused by pattern shapes or density difference from reaching the image sensor 13. The polarization devices comprise, for example, a ½ wavelength plate and a ¼ wavelength plate.

The image sensor 13 is, for example, a time delayed integration sensor (TDI sensor), which outputs shading image signals in response to the brightness (thick or thin) of the reflecting beam from the semiconductor wafer 1 having one exemplary pattern to be inspected. An A/D converter 14 converts the shading image signals 13a obtained from the image sensor 13 to digital signals. In other words, the stage 2 is scanned while the semiconductor wafer 1 having one exemplary pattern to be inspected is moved at a constant speed, so that a focus detection system (not shown) always detects the position of the surface to be inspected in the direction of the Z axis. The stage 2 is thereby controlled in the direction of the Z axis so that the space between the objective lens 11 and the surface to be inspected is kept constant. Then, the image sensor 13 detects brightness information (shading image signals) of the pattern formed on the semiconductor wafer with high accuracy.

The reference numeral 15 represents, for example, an 8-bit type gradation converter, which conducts logarithmic, exponential, and polynomial transformations on digital image signals outputted from the A/D converter 14 so as to correct uneven image brightness caused by interference between the laser beam and a thin film formed on the semiconductor wafer 1 during the processes. A delay memory 16 stores and delays output image signals from the gradation converter 15 for one cell, one chip or one shot constituting the semiconductor wafer 1 with a scanning width of the image sensor 13. A comparator 17 compares image signals outputted from the gradation converter 15 with image signals obtained by the delay memory 16 to detect disparities as defects. The comparator 17 compares the detected image with the image that is outputted from the delay memory 16 and delayed with an amount corresponding to a cell pitch, etc. Coordinates such as arrangement data on a semiconductor wafer 1 obtained based on design information are inputted with an input means 18 including a keyboard, a disk, etc., and thereby a CPU 19 creates and stores in a storage device 20 defect inspection data based on coordinates such as arrangement data on the semiconductor wafer 1, whose comparison results by the comparator 17 have been inputted.

The defect inspection data, if necessary, can be displayed on a display means 21 such as a display, and further outputted to an output means 22 so that defect points can be observed, for example, with other review devices. The comparator 17 comprises, for example, a circuit for positioning images, a differential image detection circuit of positioned images, a disparity detection circuit for digitalizing differential images, and a feature extraction circuit for extracting areas and lengths, coordinates, and other factors from the digitalized outputs.

In addition, the configuration of the low coherent optical unit 6 of the lighting optical machine is described. In general, the laser has coherence properties, and laser-lighting on a wafer may be a cause for generating speckle noise from a circuit pattern. Thus, in the case of laser-lighting, it is necessary to reduce coherence.

Either of temporal or spatial coherence can be reduced for reducing the coherence. In the present invention, a laser beam is two-dimensionally scanned by two scanning mirror mechanisms 71 and 74, which are approximately orthogonal to each other and whose reflecting faces revolve in the direction indicated by the arrow as shown in FIG. 3., to reduce spatial coherence.

The low coherent optical unit 6 is described in detail by further referring to FIG. 2. The laser beam L1 is emitted from the laser beam source 3 and expanded to a certain size by the beam expander 5 to become a parallel pencil, which is reflected by the scanning mirror mechanism 71, converged with the lens 72, and then made to become a parallel pencil again with the lens 73. After the parallel pencil is reflected by the scanning mirror mechanism 74, it is converged on the center 11a of the objective lens with the lens 7. The mirrors of the scanning mirror mechanisms 71 and 74 are in conjugate positions relative to the surface of the wafer 1. The scanning mirror mechanisms 71 and 74 have oscillating mirrors that revolve or oscillate with electric signals, and the laser beam L1 is thereby two-dimensionally scanned on the pupil of the objective lens 11. Examples of the electric signals to be inputted into the scanning mirror mechanisms 71 and 74 include triangular waves and sinusoidal waves, and variations of the frequency or amplitude of the inputted electric signals enables the scanning of various shapes on the pupil 11a of the objective lens 11.

As described above, the beam polarization mechanism and beam expander adjustment mechanism are provided relative to the laser lighting optical system. Since the lighting optical mechanism is stored in the housing, an operator can adjust the beam without directly touching the optical system and there is no fear that the beam would leak to the outside, resulting in safe operations. This allows the operator to be free from operations in a narrow space, so that safer operations are assured.

In addition, a beam spot positioning sensor or a camera for observing beam profile is provided to automatically control the beam polarization mechanism and beam expander adjustment mechanism, so that a stable beam can constantly be applied to an object to be measured.

EFFECT OF THE INVENTION

The present invention provides a lighting optical machine and a defect inspection system that are highly reliable and safe when a laser beam is used as a light source.

All publications, patents and patent applications cited herein are incorporated herein by reference in their entirety.

What is claimed is:

1. A defect inspection apparatus comprising:
a housing, wherein the housing accommodates a laser beam source, a beam deflection mechanism enabling a beam emitted from the laser beam source to be reflected so that the beam travels in the direction almost parallel to the beam emitted from the laser beam source, a beam expander for converting the beam to a parallel beam having a larger cross-sectional area, an objective lens, through which the parallel beam is reduced and applied to the surface of a sample;
a first control mechanism for controlling the beam polarization mechanism;
a second control mechanism for controlling the beam expander;
a first beam splitter for splitting the parallel beam in the light passage from beam expander to the objective lens into at least two split parallel beams;
a second beam splitter for further dividing at least one of the split parallel beams into at least two divided parallel beams;
a beam profile observation camera for observing the beam intensity profile of the cross-section of a first of the divided parallel beams;
a convergence lens for converging a second of the divided parallel beams;
a beam spot positioning sensor for detecting the position of a spot image converged with the convergence lens; and
an automatic control means for automatically controlling either or both of the first control mechanism and the second control mechanism on the basis of either or both of respective output signals from the beam profile observation camera, including information of the cross-sectional diameter of the beam, and from the beam spot positioning sensor, including information of the beam position displacement.

2. The defect inspection apparatus as set forth in claim 1 further comprising:
an optical image observation mechanism for forming an enlarged image of the sample irradiated with the second divided parallel beam; and
an image comparison mechanism for comparing images of two areas on the sample obtained by the optical image observation mechanism to detect a defect.

* * * * *

UNITED STATES PATENT AND TRADEMARK OFFICE
CERTIFICATE OF CORRECTION

| | |
|---|---|
| PATENT NO. | : 7,133,127 B2 |
| APPLICATION NO. | : 10/612148 |
| DATED | : November 7, 2006 |
| INVENTOR(S) | : Masami Iizuka et al. |

It is certified that error appears in the above-identified patent and that said Letters Patent is hereby corrected as shown below:

In the Abstract, the following are corrected:

Lines 4-5, "polarization" should read --deflection--; and

Line 13, "polarization" should read --deflection--.

In the Specification, the following are corrected:

Column 2, line 6, "polarization" should read --deflection--;

Column 2, line 55, "polarization" should read --deflection--;

Column 2, line 56, "polarization" should read --deflection--;

Column 2, line 58, "polarization" should read --deflection--;

Column 3, line 20, "polarization" should read --deflection--;

Column 4, line 5, "polarization" should read --deflection--;

Column 5, line 57, "polarization" should read --deflection--; and

Column 6, line 6, "polarization" should read --deflection--.

In the Claims, the following is corrected:

Claim 1, column 6, lines 27-28, "polarization" should read --deflection--.

Signed and Sealed this

Sixth Day of November, 2007

JON W. DUDAS
*Director of the United States Patent and Trademark Office*